(12) United States Patent
Zirps et al.

(10) Patent No.: US 7,093,813 B1
(45) Date of Patent: Aug. 22, 2006

(54) APPARATUSES FOR SUPPORTING MEDICAL EQUIPMENT AND METHODS OF ADJUSTING SUPPORT DEVICES

(75) Inventors: Christopher T. Zirps, Sharon, MA (US); Andrew W. Marsella, Boston, MA (US); Salvatore J. Dedola, New Kensington, PA (US)

(73) Assignee: MEDRAD, Inc., Indianola, PA (US)

( * ) Notice: Subject to any disclaimer, the term of this patent is extended or adjusted under 35 U.S.C. 154(b) by 0 days.

(21) Appl. No.: 10/927,425

(22) Filed: Aug. 26, 2004

(51) Int. Cl.
*A47H 1/10* (2006.01)

(52) U.S. Cl. .................................... 248/327

(58) Field of Classification Search ............... 248/317, 248/323, 327, 333
See application file for complete search history.

(56) References Cited

U.S. PATENT DOCUMENTS

| | | | |
|---|---|---|---|
| 2,618,422 A * | 11/1952 | Marchionda | ................. 53/241 |
| 4,487,389 A | 12/1984 | Ziegler | |
| 5,379,977 A * | 1/1995 | Ronn et al. | ............. 248/277.1 |
| 5,383,858 A | 1/1995 | Reilly et al. | |
| 5,664,687 A * | 9/1997 | Liatti | ........................... 211/17 |
| 6,095,468 A | 8/2000 | Chirico et al. | |
| 6,349,512 B1 * | 2/2002 | Berkey et al. | ............. 52/126.6 |
| 6,364,268 B1 | 4/2002 | Metelski | |
| 6,382,577 B1 | 5/2002 | McCoy et al. | |

OTHER PUBLICATIONS

"MaVig Counterpoise Systems Installation and Service Manual," Document # 87750-T-113 Rev. E, Distributed be Medrad, Inc. (at least as early as Aug. 2003).

* cited by examiner

*Primary Examiner*—Ramon O Ramirez
(74) *Attorney, Agent, or Firm*—Gregory Bradley; Henry Bartoney, Jr.; James Stevenson

(57) ABSTRACT

Apparatuses for supporting medical equipment are provided. Some apparatuses provide a support arm comprising a resilient assembly. The resilient assembly preferably comprises a detent and receives force imparted upon the support arm. Essentially, the assembly limits stress imparted upon the support arm and any other structure that the support arm is operatively connected to thereby making the apparatuses more durable. Another apparatus provides a collet for preventing a support arm from sliding from a housing. Yet another apparatus provides spacers than can be used to virtually extend the length of a support arm. Methods of adjusting a support arm are also provided.

3 Claims, 13 Drawing Sheets

260

APPARATUSES FOR SUPPORTING MEDICAL EQUIPMENT AND METHODS OF ADJUSTING SUPPORT DEVICES

BACKGROUND OF THE INVENTION

The present invention relates to a support device for the support of medical equipment, and to methods of use for the support device.

Space is a commodity. This has never been truer for medical environments, where desks are cluttered, offices are cramped, and floor space is scant. Specifically in radiology suites, once the patient table, chairs, cabinets, and various large equipment such as a scanner is placed in the room, there is little room for the patients, radiologists, and doctors to move around. Despite the fact that floor space is scarce, ceiling space and wall space is often abundant. As a result, many firms have produced a variety of different structures to support medical equipment that are capable of connecting to a ceiling or wall.

For example, U.S. Pat. No. 6,364,268, filed on Jun. 29, 2000, the disclosure of which is incorporated herein by reference, provides a ceiling mount having two vertical supports, one for a microscope and the other for a control system. U.S. Pat. No. 6,095,468, filed on Mar. 27, 1998, the disclosure of which is incorporated herein by reference, provides an apparatus for supporting a service column from a ceiling.

It is not necessary, however, to mount these support devices on a ceiling, as walls are often preferable. In general, there is a tradeoff between wall and ceiling mounted support devices. Ceiling mounted devices are more difficult to service, repair and adjust, whereas wall mounted devices are more likely to obstruct a person moving around the room. A wall mounted support device is provided in U.S. Pat. No. 4,487,389, filed on Nov. 17, 1982, the disclosure of which is incorporated herein by reference.

In medical institutions and radiology suites, one of the most common pieces of medical equipment that is hung from a support device is an injector head, similar to the injector head disclosed in U.S. Pat. No. 5,383,858, the disclosure of which is incorporated herein by reference. An injector delivers fluid to a patient, and injectors are used in a wide variety of medical procedures. To save space in hospital rooms, operating rooms, and radiology suites, many medical institutions use support devices that can either be wall or ceiling mounted to suspend injector heads.

Furthermore, these support devices can be either electronically controlled or manually controlled. For example, the position of the support device disclosed in previously mentioned U.S. Pat. No. 6,095,468 and U.S. Pat. No. 6,364,268 is controlled electronically by a control system. U.S. Pat. No. 6,382,577, filed on Dec. 15, 1999, the disclosure of which is incorporated herein by reference, on the other hand, discloses a manually controlled articulated support arm to support a computer monitor.

In terms of supporting medical equipment, there are several factors to take into consideration. First of all, the support device must be able to adequately support the load of the medical equipment that the device intends to support. For an injector, a typical piece of medical equipment, the standard load is generally in the range of 10 to 50 pounds. The support device must not only be able to adequately support the device, but must also be able to withstand the rigors of everyday use while bearing such a load. For example, the support device must not be susceptible to vertical, horizontal, or torsional force if the support device is inadvertently bumped or moved while bearing the medical equipment.

Furthermore, the support device must be able to freely move the piece of medical equipment to a position in which it will not interfere with standard operation in the room if the medical equipment is not to be used. In addition, the support device must be able to move the piece of equipment to a position in which the piece of medical equipment can be efficiently utilized without the support device interfering with the medical procedure.

The support device must also provide relatively stable placement of the medical equipment once it is moved into desired position.

Yet another consideration is control. There is generally a tradeoff between manual and electronic control of the support device. Electronic control of the support device typically results in more accurate placement of the support device, while manual control of the support device is typically more time-efficient.

As of yet, these issues have not been completely met by the prior art. Mavig's *Counterpoise Systems Installation and Service Manual*, the disclosure of which is incorporated herein by reference, discloses standard medical equipment bearing support device. The device is a manually controlled support device that has an adjustable ceiling mount along with a system of three support arms. While this device is clearly a step in the right direction, all of the aforementioned issues have not yet been met by the current technology.

In fact, one of the most significant obstacles to overcome in designing an effective support device is the question of durability. Specifically with regard to many manual support devices, there is a high rate of failure of the devices after only a short period. In general, many of these devices simply cannot withstand the rigors of everyday use as the joints of the support devices regularly falter.

Finally, but not any less significantly, these devices are difficult to install and operate. In many cases, it requires multiple people to effectively install a support device. With the medical industry overworked and understaffed as it is, ease of use is a priority for all modern support devices.

Clearly the current technology for supporting medical equipment through the use of a support device in medical procedures imposes undue costs, and promotes inefficiency in medical institutions with regard to medical procedures.

For the foregoing reasons, there is a need for new apparatuses, systems, and methods, for supporting medical equipment through the use of a support device in medical procedures.

SUMMARY OF THE INVENTION

The present invention provides, in one aspect, an apparatus for supporting medical equipment. The apparatus comprises a first support arm operatively connected to a support structure, the first support arm comprising an assembly to limit force imparted upon the first support arm.

According to another aspect of the present invention, there is further provided an apparatus for supporting medical equipment. The apparatus comprises a first support arm operatively connected to a support structure and an assembly disposed on the first support arm to limit force imparted upon the support arm.

Such a device could be adapted to support virtually any form of medical equipment including, but not limited to, a medical injector, a viewing screen, a control console, a computer terminal, or lights.

One skilled in the art will recognize that there is a variety of ways that such a device could be aligned in a medical institution. In one preferred embodiment, the support arm is aligned substantially vertically, but in another preferred embodiment, the support arm is aligned substantially horizontally. The device could also simply be aligned at an angle neither substantially vertical nor substantially horizontal.

The different ways in which the support device could be aligned calls for a variety of ways in which the support device could be positioned in a room. By a preferred embodiment, the support structure is a ceiling, but one skilled in the art will recognize that virtually any rigid structure, such as a wall, bed frame, or desk, could serve as the support structure for the present invention.

Optimally, the support device would be connected to a mooring, which may be concrete, that is disposed in the support structure. The mooring, while not necessary, provides additional support for the support device. In applications intended to support particularly heavy objects, such as a medical injector, it is recommended that a mooring be used.

In another preferred embodiment, the support device may further comprise a housing. In one embodiment, the support arm is at least partially disposed inside of the housing. Such a housing can be used for added support and stability for the support arm. For example, the housing may serve as part, or all, of a mount.

Another aspect of the present invention provides an apparatus for supporting medical equipment. The apparatus comprises a first support arm operatively connected to a support structure, the first support arm comprising an assembly to limit force imparted upon said support arm, wherein the assembly comprises a detent.

The detent, which is disposed inside of the assembly, is operable to allow the support arm to partially hinge at the assembly. In essence, the detent serves to limit the application of force and provide the user with tactile and visual indication of overload. In a preferred embodiment, the assembly is a partially hollow and substantially cylindrical metal sleeve. The interior of the sleeve is shaped to receive a metal rod, which serves as the detent. In this embodiment, if a great enough force is imparted upon the support arm from any direction, the support arm partially hinges and slides against the detent. After the force dissipates, the detent mechanism forces the assembly to return to its original resting place, and the support arm returns to its original position. Thus, the activation of the detent provides indication of excess force imparted upon the support arm.

One skilled in the art will recognize that there are many different ways in which to construct a detent inside of an assembly to receive motion imparted upon the support arm. There are also a plethora of objects that could serve as an effective detent. For example, a ball bearing, wedge, or toggle can serve as an effective detent. Virtually any device that can be used for positioning and holding one mechanical part in relation to another so that the device can be released by force applied to one of the parts will fulfill the purpose of the detent. Furthermore, the use of different objects as the detent allows the assembly of the present invention to be modified for the application in question.

In another preferred embodiment, the detent is energized by a spring, which makes the support arm even more resilient. The amount of energy applied by the spring can provide varying degrees of protection to limit damaging forces to the remainder of the support system. In this fashion, the assembly structure can be tuned or modified to suit a specific application. Energy can be applied to the detent by other mechanisms such as compressible fluid members, air cylinder, elastomeric members, shock absorbing devices, and gravity.

In addition, one skilled in the art will recognize that the assembly need not be partially hollow, substantially cylindrical, or metal. For example, the assembly may be constructed of two substantially conical pieces that engage each other at their respective tips. As long as the objects are arranged to hinge they can be fitted for use in the assembly of the present invention. Furthermore, virtually any substantially rigid material, such as metal, plastic, wood, or composite, will serve as an effective detent.

According to another aspect of the present invention, an apparatus comprises a first support arm operatively connected to a support structure and an assembly disposed on the first support arm to receive force imparted upon said support arm, the assembly comprising a detent.

By yet another aspect of the present invention, an apparatus comprises a housing operatively connected to a support structure and a first support arm adapted to at least partially fit within the housing and positioned to extend outwardly from the housing. The apparatus further comprises a spacer adapted to fit at least partially within the housing to allow the first support arm to further extend outwardly from the housing.

In one preferred embodiment, the housing serves as a mount, which may be connected to a mooring disposed inside of the support structure.

In another preferred embodiment, the spacer is a substantially cylindrical plastic piece that can be loaded into the housing. One skilled in the art will recognize that such a spacer could be loaded into the housing in a variety of ways. For example, the spacer could be loaded into the housing at one of the ends of the housing. Likewise, the spacer could be loaded at some point on the body of the housing by virtue of an opening that may or may not comprise a door.

One skilled in the art will further recognize that a spacer of the present invention need not be substantially cylindrical or plastic. The spacer could just as easily be a wood or metal cube capable of fitting inside of the housing.

Essentially, the housing can be capable of accommodating a substantially large portion of the support arm, meaning that nearly all of the support arm can be disposed inside of the housing. The housing can also be capable of accommodating a substantially small portion of the support arm, meaning that nearly all of the support arm can be disposed outside of the housing. A spacer can be loaded into the housing to fill a portion of the housing so that removing or adding the spacer allows the housing to accommodate more or less of the support arm, respectively.

In a preferred embodiment of the present invention, the spacers are inserted between the support arm and the portion of the housing that is connected to a support structure. For example, the spacers can be placed inside of a ceiling mount between the ceiling and the support arm, which is also disposed at least partially inside of the mount. In such an arrangement, the spacers can serve to prevent upward movement of the support arm if vertical force is applied to a different portion of the support structure. Furthermore, such an arrangement also serves as storage for the spacers to ensure availability if future adjustment is required.

In a preferred embodiment, more than one spacer is provided. A set of spacers allows the device to be more variably extendable. Furthermore, the smaller each spacer is allows the apparatus to extend by smaller intervals, and increases the flexibility of installation and operation provided by the apparatus.

According to yet another aspect of the present invention, an apparatus comprises a housing operatively connected to a support structure and a first support arm adapted to at least partially fit within the housing and positioned to extend outwardly from the housing. The apparatus further comprises a collet adapted to fit at least partially within the housing, the collet also adapted to receive the first support arm to prevent the first support arm from sliding linearly or rotationally inside of the collet.

In a preferred embodiment, the collet is disposed in the housing at the portion of the housing that the support arm extends from. The collet is preferably a substantially tapered, substantially flexible sleeve constructed of substantially semi-rigid plastic. The support arm is adapted to fit at least partially inside of the collet. Because the collet is substantially tapered and substantially flexible, the support arm fits tightly against the interior wall of the collet. This makes it difficult for the support arm to slide within the collet, and deliberate force must be imparted upon the support arm for the support arm to slide in the collet. Furthermore, in this embodiment, the outside wall of the collet fits substantially tightly against the housing so that it is difficult for the collet to slide out of or rotate within the housing.

One skilled in the art will recognize that the collet need not be flexible or constructed of plastic. For example, the collet may be constructed of metal and adjusted by a screw lock or screw so that the collet could be tightened by hand or a simple machine such as a screw driver.

By yet another aspect of the present invention, an apparatus comprises a housing operatively connected to a support structure and a first support arm adapted to at least partially fit within the housing and positioned to extend outwardly from the housing. Furthermore, the first support arm is adapted to prevent rotational movement of the first support arm.

In one embodiment of the present invention, the support arm is splined or keyed so that it can interact with the housing. Thereby, a projection on the support arm could be fit into a slot defined by the interior of the housing so that the support arm could not rotate inside of the housing.

By still another aspect of the present invention, an apparatus comprises a first support arm connected to a second support arm. The connection between the first support arm and second support arm is facilitated by a self-lubricating polymer bushing.

Self lubricating polymer bushings provide an effective blend of structural integrity, self lubrication, and reasonably low running friction that allows ease of movement, but enables reasonable installation constraints on the system by remaining level and plumb within plus or minus one degree.

By another aspect of the present invention, a method of installing a medical support device comprises (1) placing a housing defining a proximal end and a distal end against a mounting surface adapted to interact with said distal end of the housing, and (2) rotating the housing to secure the housing against the mounting surface. This method of installation makes it possible for a single person to install an entire support structure.

In a preferred embodiment of the present invention, the mounting surface can be a plate defining channels into which projections defined by the distal end of the housing can be inserted. Once the projections are placed in the channels, the housing could be secured against the plate by simply rotating the housing.

In a preferred embodiment of the present invention, the method further comprises further securing the housing against the plate by utilizing screws, which can be driven through the distal end of the housing and into the mounting surface.

By another aspect of the present invention, a method of adjusting a first support arm is provided. The method comprises (1) inserting a first support arm into a housing comprising a proximal end and a distal end so that the first support arm extends outwardly from the distal end of the housing, and (2) placing at least one spacer between the first support arm and the distal end of the housing to further extend the first support arm outwardly from the housing.

In a preferred embodiment of the method, the method further comprises removing at least one spacer from the housing. In another preferred embodiment, the method further comprises operatively connecting medical equipment to the first support arm. By yet another preferred embodiment, the method further comprises engaging a first spacer with a second spacer.

By yet another aspect of the present invention, a method of adjusting a first support arm comprises (1) separating a first support arm from a structure wherein the first support arm comprises a proximal end and a distal end, and (2) placing spacers in between the proximal end of the first support arm and the structure to further extend the first support arm outwardly from the structure.

In a preferred embodiment, the structure is a second support arm. In another preferred embodiment, the method further comprises engaging a first spacer with a second spacer.

By yet another aspect of the present invention, a method of adjusting a first support arm comprises (1) inserting at least a portion of a first support arm into a housing comprising a proximal end and a distal end so that the first support arm extends outwardly from the distal end of the housing, and (2) placing at least one spacer at least partially within the housing to further extend the first support arm outwardly from the housing.

In a preferred embodiment of the method, the method further comprises opening the housing. Another preferred embodiment of the method comprises closing the housing.

The principles, operation, and features of the present invention may be better understood with reference to the drawings and the accompanying description.

DETAILED DESCRIPTION OF THE EMBODIMENTS OF THE INVENTION

The present invention generally provides apparatuses for supporting medical equipment along with methods of adjusting a support device. There are three main components provided herein. The first component is an assembly. As used herein, the term "assembly" refers to an object formed by fitting or joining components together. There are several different ways in which to align an assembly of the present invention, but in general a support arm comprises the assembly, or the assembly is disposed on the support arm. The assembly basically limits force imparted upon the support arm.

The assembly component of the present invention may, or may not, include a detent. As used herein, the term "detent" refers to a device for positioning and holding one mechanical part in relation to another so that the device can be released by force applied to one of the parts. In other words, a detent serves as a device that locks or unlocks a movement, in the case of the present invention the movement being generated by force applied to the support device.

The second main component is a collet. As used herein, the term "collet" refers to a sleeve used for holding pieces in a machine. A collet of the present invention may be incorporated into a support device in a variety of ways. The collet is usually at least partially disposed in a housing of some type. In general the collet accepts at least a portion of a support arm and prevents the support arm from sliding out of the collet.

The third main component is a spacer. A spacer of the present invention is also usually at least partially disposed in a housing of some type. There are also usually multiple spacers that act in conjunction with one another. The spacer or spacers engages a support arm and virtually extend the length of the support arm. It is particularly useful to be able to extend a support arm disposed in rooms with extraordinary dimensions. For example, if the support device is mounted on a ceiling that is higher than normal, it may be best to extend the support arm further than normal. Likewise, if the ceiling is lower than normal, it may be best to extend the support arm lesser than normal.

The methods of adjusting a support arm of the present invention relate generally to adjusting the length of the support arm via a spacer or spacers.

Figure 1:
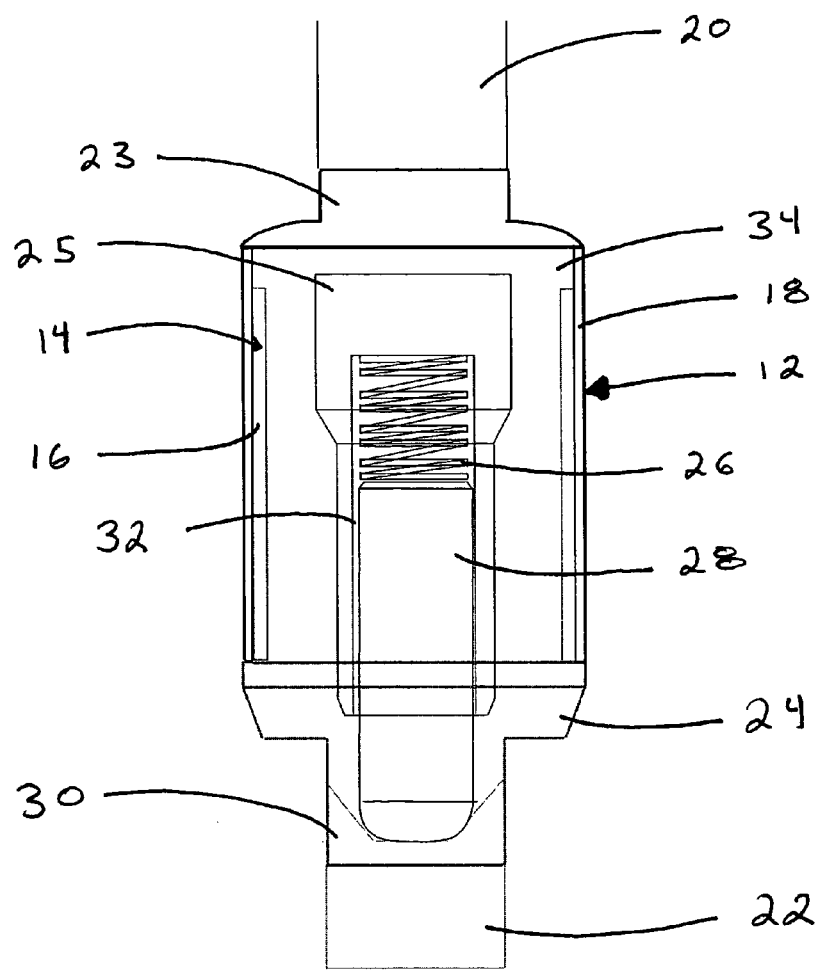
FIG. 1 illustrates a front view of an assembly of the present invention as it is used in conjunction with a support arm.

Referring now to the drawings, FIG. 1 shows a preferred embodiment of an assembly of the present invention. As illustrated, the assembly 12 is disposed on a support arm comprising the first portion 20 of the support arm and the second portion 22 of the support arm. The exterior of the assembly is comprised of three primary components: the cap 23, the cover 18, and the lower portion 24 of the body 14. The cap 23 is capable of connecting with the first portion 20 of the support arm, and the lower portion 24 of the body 14 is capable of connecting with the second portion 22 of the support arm. The cover 18 can be constructed of flexible material. Preferably, the cover 18 is rubber, polyurethane, or plastic, but one skilled in the art will recognize that virtually any substantially semi-flexible material is suitable.

Figure 2:
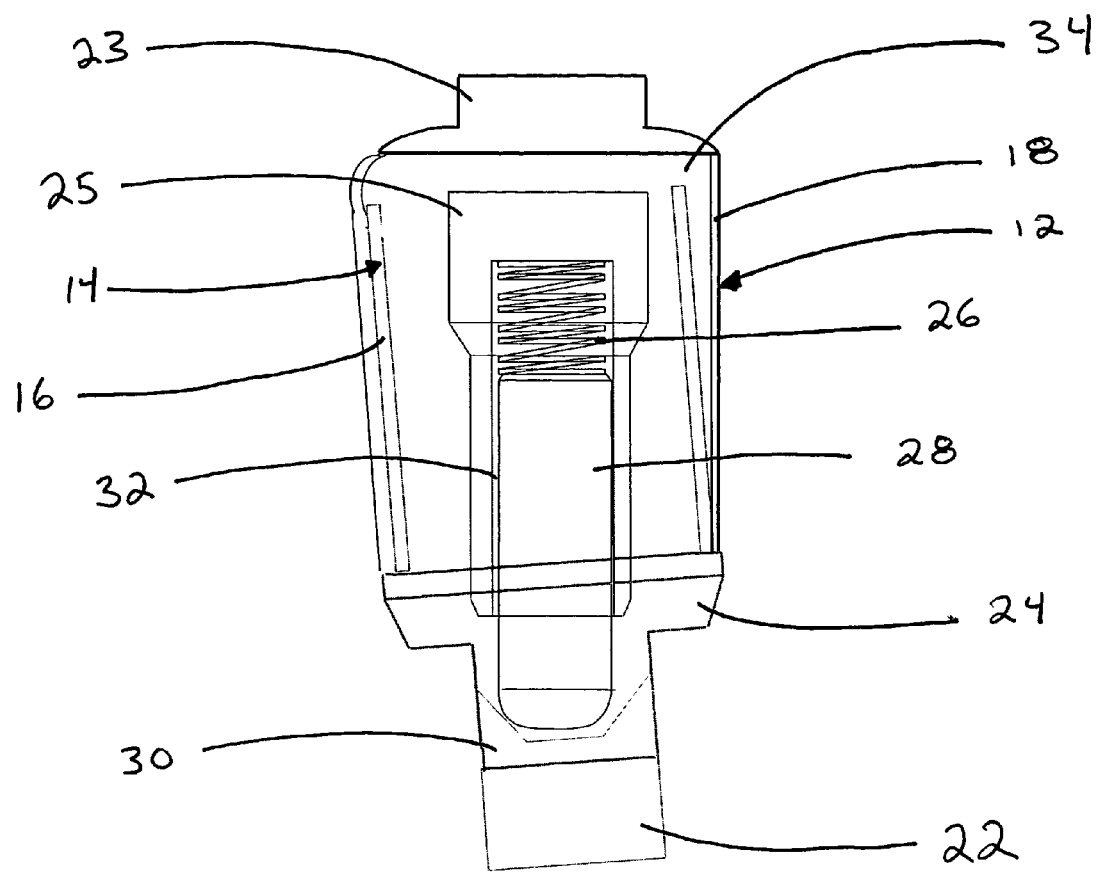
FIG. 2 illustrates a front view of an assembly of the present invention as it flexes.

The cover 18 is adapted to fit over the main portion 16 of the body 14. Furthermore, the upper portion 16 of the body 14 extends from the lower portion 24 of the body towards the cap 23, but is not connected to the cap 23. In fact, there is a small space, referred to as a pinch point 34, between the upper portion 16 of the body 14 and the cap 23. The pinch point 34 is an important feature of the assembly 12, for the pinch point 34 allows the assembly 12 to hinge. An illustration of the assembly 12 as it hinges is shown in FIG. 2.

It should also be mentioned that the cover 18 is not an essential component of the assembly 12, although it does serve several purposes. First and foremost, the cover 18 extends over the pinch point 34 so that a user of the device cannot pinch a finger as the assembly 12 hinges. Secondly, cover 18 provides a good handle with which a user can maneuver the support device.

The inner housing 25 of the assembly 12 is contained within the body 14, and defines a channel 32. A spring 26 can be loaded into the channel 32 so that it presses against the wall of the inner housing 25. Similarly, a detent 28 can also be loaded into the channel 32 so that it presses against the spring 26. The channel 32 should be constructed so that the detent 28 fits snugly in the channel 32 thereby limiting horizontal movement of the detent 28.

The detent 28 also extends from the inner housing 25 so that the end of the detent 28 rests against the flat bottom portion of a seat 30 contained in the lower portion 24 of the body 14.

The seat 30 may or may not be formed integrally with the lower portion 24 of the body 14. It is also possible for the seat 30 to be a separate piece that can be inserted into the lower portion 24 of the body 14.

One skilled in the art will recognize that the body of the assembly may deviate from this embodiment significantly. For example, instead of completely enclosing the interior assembly, the body could simply be constructed of several supports.

FIG. 2 illustrates the assembly 12 as it receives force significant enough to cause it to flex. Here, the body 14 of the assembly 12 tilts as it receives pressure. Although the body 14 tilts, the inner housing 25 does not move laterally. This means that as the body 14 tilts the flat bottom portion of the seat 30 moves away from the detent 28, and the angled wall of the seat 30 exerts vertical pressure on the detent 28 forcing the spring 26 to compress.

It is easy to see how the cover 18 protects the pinch point 34 in this illustration. In addition to providing added safety and protection by guarding against a user getting their finger caught in the pinch point 34, the cover also provides visual and tactile feedback of overload on the assembly 12. It does this because as the body 14 tilts the upper portion 16 of the body 14 presses against the semi-flexible cover 18 causing it to bulge on one side.

This means that, in essence, for the assembly 12 to tilt the force imparted upon the assembly 12 must be strong enough to overcome the resistant force of the detent 28 on the seat 30 resulting from the axial force exerted by the spring 26. This requires an excessive force that such an assembly should not meet in the course of normal operation. However, since the assembly provides indication of force that could potentially damage the device, the user is notified when the device is under excessive stress.

Figure 3:
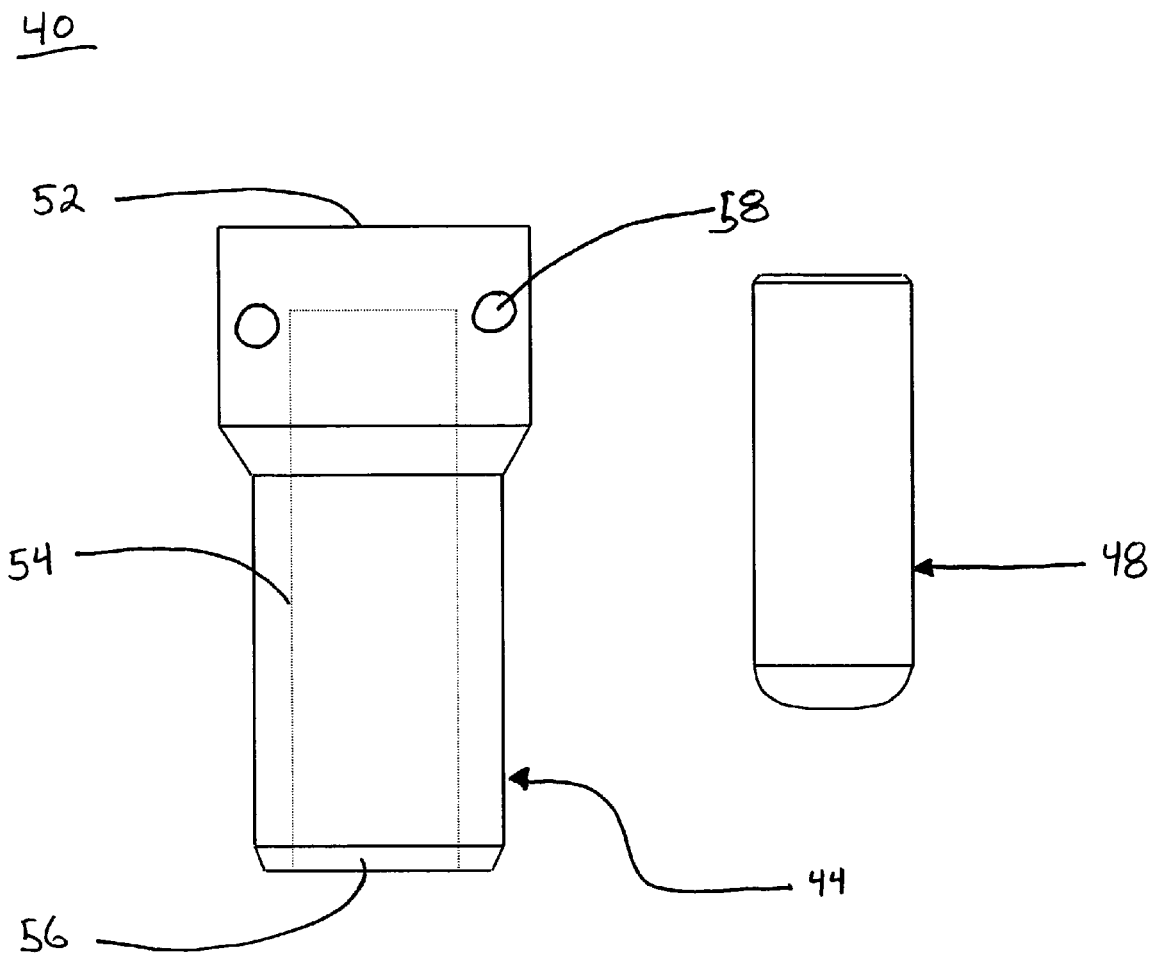
FIG. 3 illustrates an exploded view of two components of a preferred embodiment of the interior of the assembly of FIG. 1.

FIG. 3. The internal assembly 40 can be constructed of two parts: an inner housing 44 and a detent 48. The detent is placed in a channel 54 defined by inner housing 44 at the bottom portion 56 of the inner housing 44 so that the rounded edge of the detent 48 completely extends beyond the bottom 56 of the inner housing. The detent 48 should fit fairly snugly inside of the channel 54 so that the inner housing 44 and detent 48 do not move horizontally inside of the assembly.

In addition, the inner housing 44 can define a hole 58 into which a pin or screw could be inserted to secure the inner housing 44 inside of the assembly. Although the hole 58, as it is illustrated, is disposed towards the top 52 of the inner housing 44, one skilled in the art will realize that it could easily be disposed virtually anywhere on the inner housing 44. One skilled in the art will recognize a myriad of ways in which the inner housing 44 could be secured inside of the assembly, for example, the inner housing 44 could be formed integrally with another portion of the assembly, or it could even be adapted to interact with another part of the assembly.

One skilled in the art will recognize that the internal assembly 44 is fairly straightforward and could be modified significantly without deviating from the spirit of the invention. For example, a spring may be loaded into the top portion 52 of the inner housing 44. Or, the detent could be held within the inner housing 44 against a spring or elastomeric member, which could increase the durability and resiliency of the device. Furthermore, the shape and construction of the internal assembly 44 and detent 48 are both very general, and the same basic idea of constructing an assembly to receive force imparted on the support arm could be realized by deviating from this design. For example, a standard ball bearing assembly could easily be constricted to fulfill the aforementioned purpose.

Figure 4:
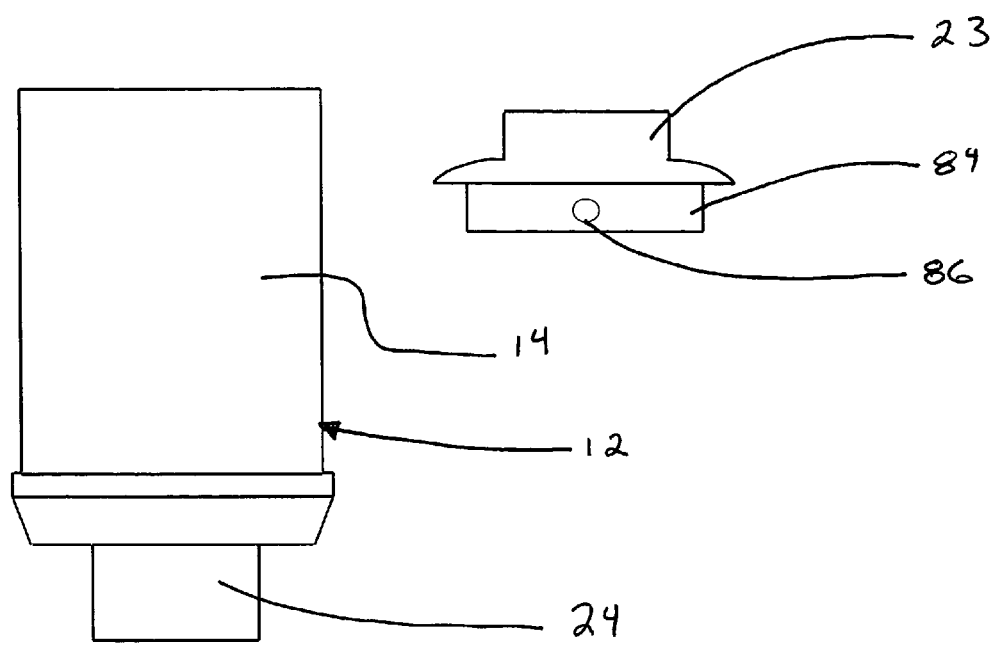
FIG. 4 illustrates an exploded view of the assembly of FIG. 1 with the cap removed.

As shown in FIG. 4, the cap 23 is here disconnected from the body 14 of the assembly 12. As is illustrated the cap 23 is capable of connecting to the body 14 of the assembly 12 at the bottom 84 of the cap 23. A simple screw lock may facilitate this connection through the hole 86 defined by the cap 23, but one skilled in the art will recognize that many types of other feasible connections would include, but not be limited to, a screw lock, a locking pin, clips, ties, binds, tape, glue, or another form of connection.

The interior of the lower portion 24 of the body 14 is also shaped to interact with the detent 48 (shown in FIG. 3). The interior of the lower portion 24 of the body 14 is concave to best interact with the shape of the detent 28 in this embodiment. One skilled in the art will recognize that the shape of the pivot is dependent on the shape of the detent. For example, if the detent is triangularly or cone shaped, then the interior of the bottom 84 of the lower portion 24 would most likely be grooved to best interact with the detent 28.

One skilled in the art will further recognize that the lower portion 24 of the body 14 does not necessarily need to be formed to interact with the detent 28. In fact, as shown in FIG. 1, the lower portion 24 of the body 14 does not interact with the detent 28. Rather, a seat, which is formed to interact with the detent 28 is inserted into the body 14 of the assembly.

Figure 5:
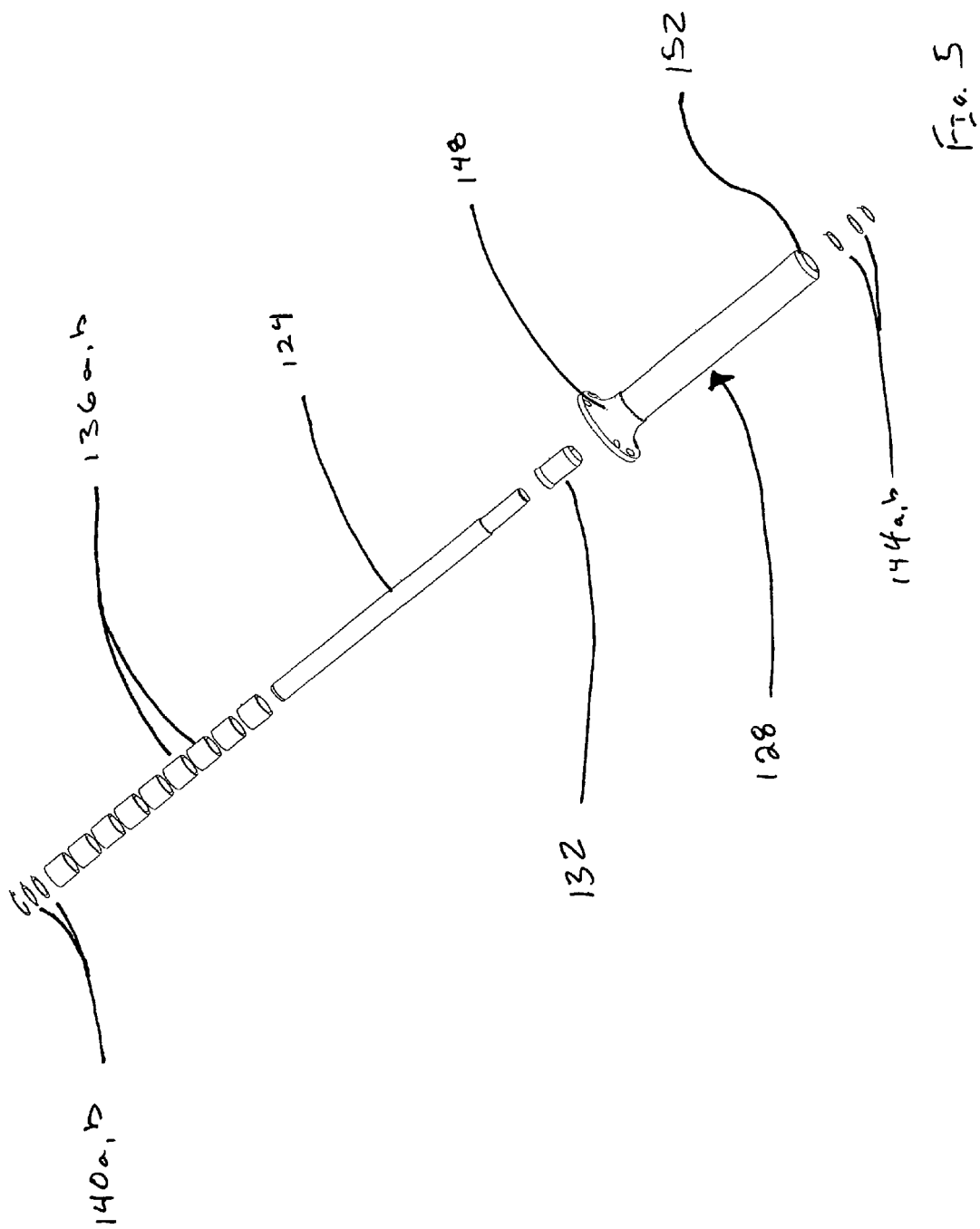
FIG. 5 illustrates an exploded isometric view of a support arm structure of the present invention.

As shown in FIG. 5, there are four basic components to the support arm and housing: the support arm 124, the housing 128, the collet 132, and the spacers 136a,b. As illustrated, the housing 128 comprises a proximal end 148 for mounting on a support structure, such as a wall or a ceiling, and a distal end 152 from which the support arm 124 extends. A standard version of a housing that acts as a ceiling mount would preferably be installed at a height of 80" to accommodate head clearance for 99% of males. Of course, this is a standard measurement, and one skilled in the art will recognize that a support device of the present invention can be mounted on a variety of support structures at a variety of heights. One skilled in the art will recognize that the housing 128 does not need to be mountable for the same basic principles of the present invention to apply. For example, a first support arm could be connected to a housing that houses a second support arm.

The collet 132 is meant to be disposed inside of the housing 128 near the distal end 152. The support arm 124 is also meant to be at least partially disposed inside of the housing 128 so that at least a portion of the support arm 124 extends from the distal end 152 of the housing 128. The collet 132 is sleeve shaped, and when the support arm 124 is disposed inside of the housing 128 so that at least a portion of the support arm 124 extends from the distal end 152 of the housing, a portion of the support arm 124 is also disposed in the collet. The collet 132 is tapered and flexible to prevent the support arm 124 from sliding or rotating within the housing 128. The collet 132 is generally made of semi-rigid material such as plastic, and the leading edge of the collet 132 engages the interior edge of the distal end 152 of the housing to prevent the collet 132 from sliding out of the housing 128. The tapered construction of the collet 132 provides enough support to prevent the support arm 124 from sliding out of or rotating within the housing 128.

In a preferred embodiment, the collet 132 is constructed of polycarbonate, which is a material generally characterized by high-impact strength, light weight, and flexibility. In another preferred embodiment, the collet 132 is constructed of polyurethane, which is a resin that can vary widely in flexibility, and is used in tough chemical-resistant coatings, adhesives, foams, paints, plastics, or rubbers.

One skilled in the art will recognize that there are many materials available to suitably construct an effective collet such as plastic, metal, composite, or some other material. However, one skilled in the art will recognize that it is imperative that the collet be at least partially flexible so that it can fit tightly against the support arm. Therefore, for this to be done with metal or wood, the collet would need slight modifications. For example, if the collet were to be constructed of aluminum, then it would be preferable to cut axial slots around the collet to allow the collet to partially collapse. Furthermore, one skilled in the art will realize that the collet 132 does not necessarily need to be positioned at the distal end 152 of the housing 128. For example, the collet 132 could be located somewhere along the interior length of the housing 128.

The collet 132 is secured inside of the housing 128 as the leading edge of the collet 132 wedges against the interior wall of the distal end 152 of the housing 128. One skilled in the art will recognize that the mount is general and secondary to the present invention. The present invention is not necessarily dependent on the mount, but the present invention can be modified to work with virtually any mounting mechanism. Furthermore, one skilled in the art will recognize that it is not relevant what kind of support structure the apparatus is operatively connected to. This device or modifications thereof can work with a support apparatus that is operatively connected to any support structure including, but not limited to, a wall, ceiling, desk, bed frame, table, chair, stand, or other support structure.

Spacers 136a, b are also provided. These spacers 136a, b can be loaded or removed from the proximal end 148 of the housing 128 to increase or decrease how far the support arm 124 extends from the distal end 152 of the housing 128. Abutment member or members such as locking ring 140a and/or washers 140b can be attached to support arm 124 at a rearward end thereof to abut a rearward surface of one of the spacers 136a,b to position support arm 124 within the housing 128. Loading spacers 136a,b into the proximal end 148 of the housing 128 will increase the amount the support arm 124 extends from the distal end 152 of the housing 128. Removing spacers 136a, b from the proximal end 148 of the housing 128 will decrease the amount the support arm 124 extends from the distal end 152 of the housing 128.

Using spacers 136a,b, makes the length of the support arm 124 adjustable so that the support arm 124 can be adapted to work efficiently under more circumstances. For example, if the support device is hung from a ceiling, the support arm 124 can be retracted so that a taller person does not inadvertently run into the support arm 124. The support arm 124 could additionally be extended if a doctor is shorter and needs the medical equipment lower to the ground. In situations where the support device is mounted on a wall, the support arm 124 may be retracted to keep the support arm 124 out of the way of someone that is walking around the table. Furthermore, the support arm 124 could be extended from the wall so that the medical equipment is in closer proximity to the patient.

Standard spacers of the present invention are 2" in length. These standard spacers allow a standard support arm when used in conjunction with a standard housing acting as a ceiling mount to adjust the overall length of the support arm between 18" and 46". Furthermore, for the standard housing to be installed at a preferable height of 80", the embodiment of FIG. 5 would accommodate ceiling heights of 8'2" to 10'6". One preferred embodiment provides a set of nine spacers, although virtually any number of spacers could be used in conjunction with a support arm and a housing as long as the support arm and/or the housing is capable of at least partially accepting the spacers. Of course, these are standard measurements, and one skilled in the art will recognize that the sizes and lengths of the various components are provided only as preferable embodiments. The spacers, support arm, housing, and other components, can be feasibly designed in a variety of configurations at a variety of specifications.

One skilled in the art will recognize that spacers of the present invention do not necessarily need to be loaded into the proximal end of a housing and that the housing does not necessarily need to be constructed in the same shape as housing 128. By constructing a lever that partially opens or partially closes the distal end of a housing, the collet and/or spacers could just as easily be loaded into the distal end of the housing. Furthermore, by constructing a housing with a door along the length of the housing, the spacers and/or collet could easily be loaded anywhere along the length of the housing.

Figure 6:
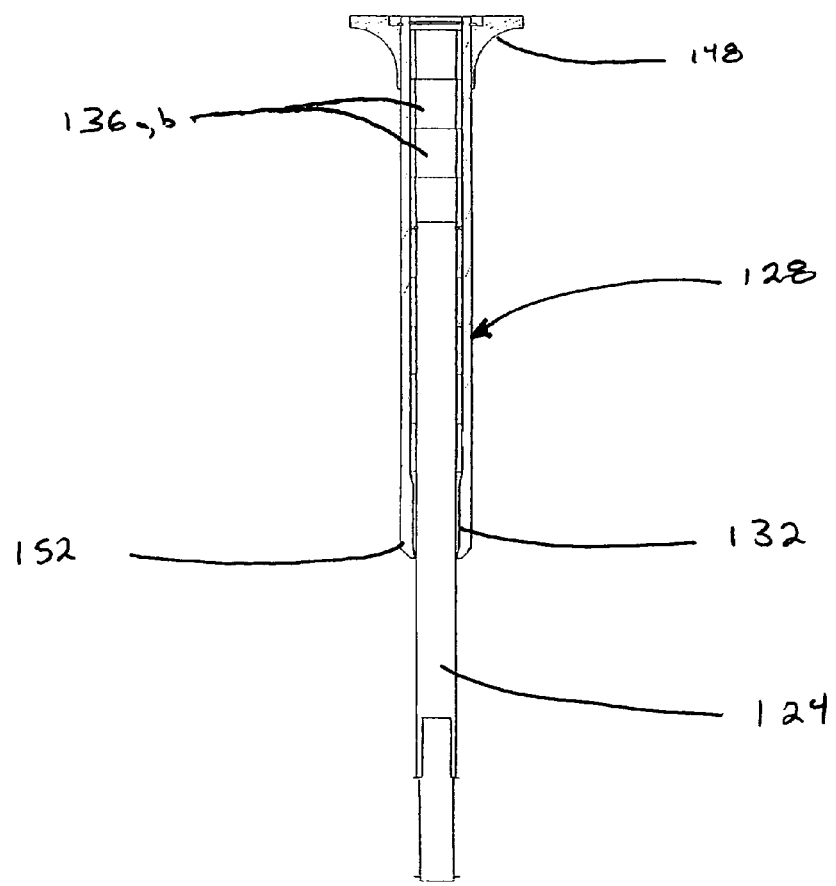
FIG. 6 illustrates a cross sectional view of the support arm structure of FIG. 5 in an unexploded state.

As shown in FIG. 6, the housing 128, support arm 124, collet 132, and spacers 136a,b, are all the same as in FIG. 5, only a different view is shown. As is illustrated, the support arm 124 is at least partially disposed within the housing 128, and a portion of the support rod 128 extends from the distal end 152, and the collet 132 prevents linear or rotational movement relative to the support arm 124. The spacers 136a,b are disposed between the support arm 128 and the proximal end 148 of the housing 128 and loading or unloading spacers 136a,b will increase or decrease how far the support arm 124 extends from the distal end 152 of the housing 128, respectively.

Figure 7:
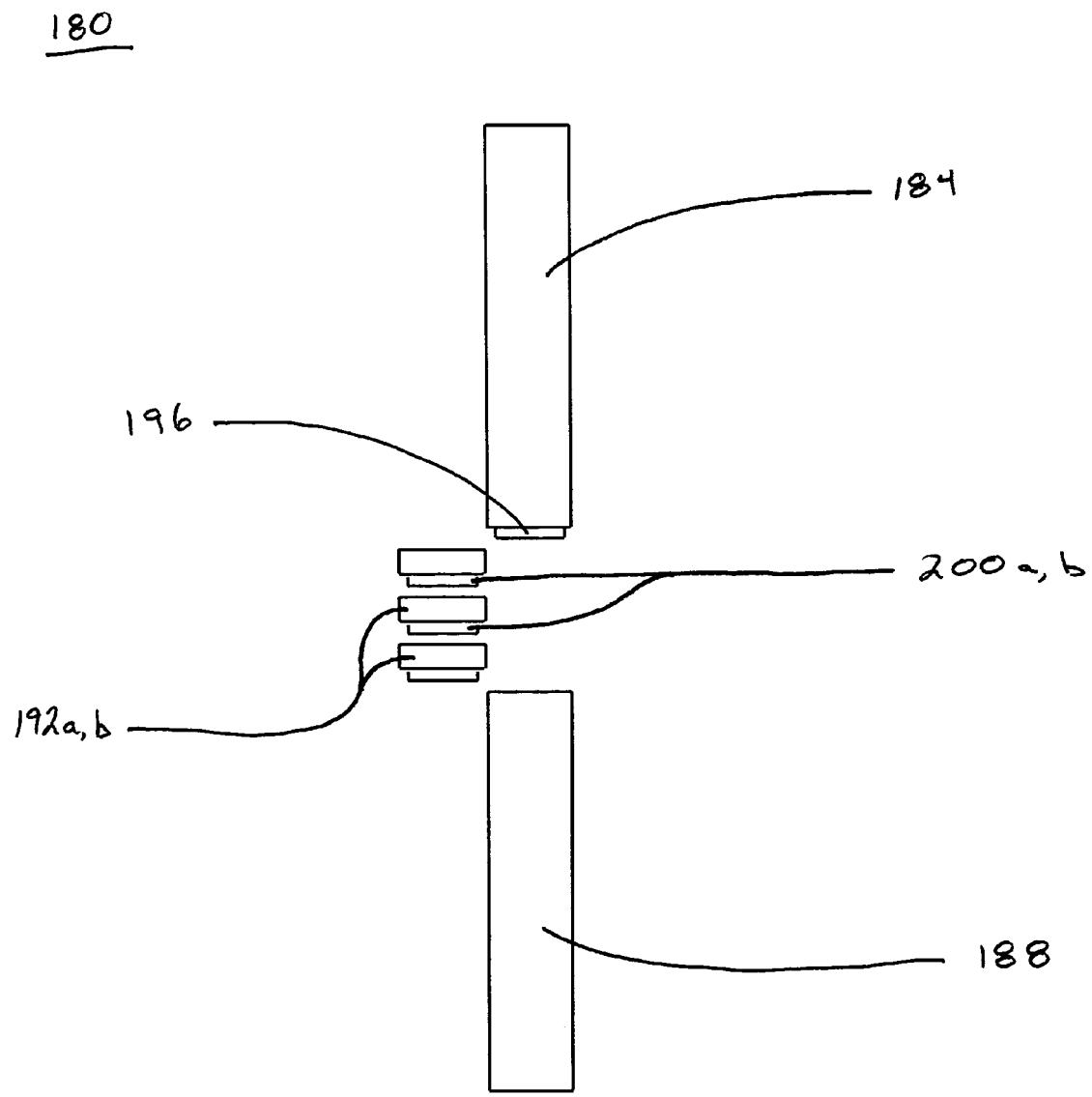
FIG. 7 illustrates an alternate embodiment of the support arm structure shown in FIG. 5 and FIG. 6.

As shown in FIG. 7, in this embodiment the spacers 192a,b are not disposed inside of a housing, but rather interact with the first portion 184 of the support arm and second portion 188 of the support arm to either increase or decrease the length of the support arm. The first portion 184 of the support arm comprises the male portion 196 of a screw lock, whereas the second portion 188 of the support arm comprises the female portion of a screw lock. Thus, the first portion 184 of the support arm can easily be connected to the second portion 188 of the screw lock to maintain the original length of the support arm.

Each of spacers 192a,b comprises the male portion 200a,b of a screw lock and the female portion of a screw lock. By aligning the male portion 200a,b of the screw lock on a spacer 192a,b with the second portion 188 of the support arm, and tightening both the spacer 192a,b into the second portion 188 of the support arm and the first portion 184 of the support arm into the spacer 192a,b, a spacer can be added.

Spacers 192a,b are added by aligning male portions 200a,b of the screw lock with the female portions of the screw lock and then tightening the lock. The male portion 200a,b of the screw lock of the spacer 192a,b adjacent to the second portion 188 of the support arm interacts with the female portion of the screw lock on the second portion 188 of the support arm. The female portion of the screw lock of the spacer 192a,b adjacent to the first portion 184 of the support arm interacts with the male portion 196 of the screw lock on the first portion 184 of the support arm.

Figure 8:
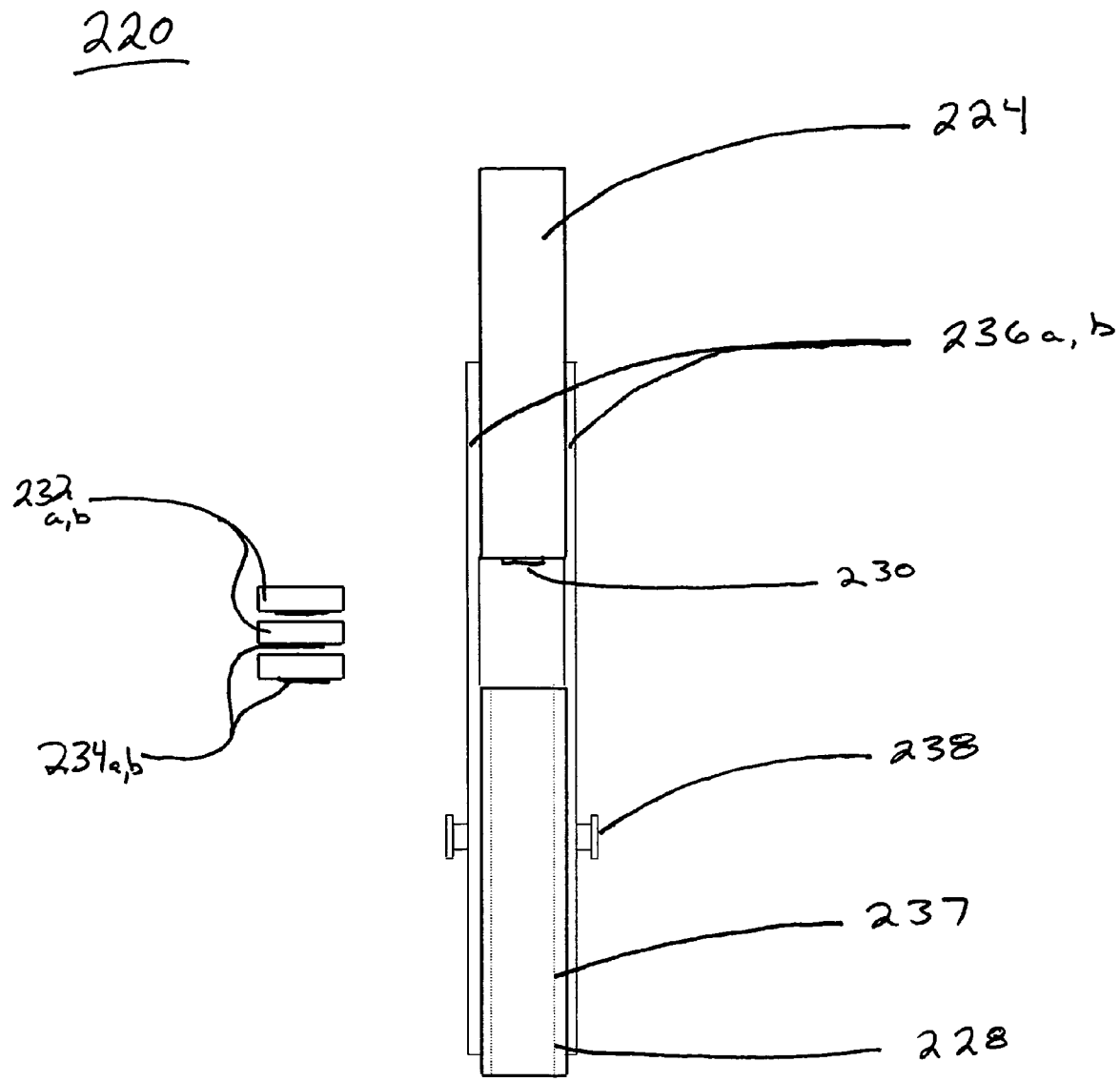
FIG. 8 illustrates an alternate embodiment of the support arm structure shown in FIG. 5 and FIG. 6.

FIG. 8. The first portion 224 of the support arm is connected to the second portion 228 of the support arm by two supports 236a,b. The two supports 236a,b are fixed on one end to the first portion 224 of the support arm. Each support 236a,b has a channel 237 cut into it so that the support can slide around a locking pin 238 that allows the respective support to lock into a position on the second portion 228 of the support arm. Thus, when the locking pin 238 is loosened it is capable of lengthening or restricting the amount of space between the first portion 224 of the support arm and the second portion 228 of the support arm.

This allows the second portion 228 of the support arm to separate from the first portion 224 of the support arm.

As illustrated, a clip 230 is visible as it is disposed on the first portion 224 of the support arm. The clip 230 is capable of interacting with a groove (not shown) defined by the second portion 228 of the support arm to help hold the first portion 224 of the support arm and the second portion 228 of the support arm together.

However, spacers 232a,b are provided to make the support arm extendable. If the second portion 228 of the support arm is separated from the first portion 224 of the support arm, one or more spacers 232a,b are placed in between the supports 236a,b. Each spacer 232a,b defines a groove (not shown) identical to the groove defined by the second portion 228 of the support arm. Each spacer 232 a,b also comprises a clip 234a,b identical to clip 230 disposed on the first portion 224 of the support arm. The clips 234a,b of the spacers 232a,b are capable of interacting with other spacers 232a,b or the second portion 228 of the support arm. The grooves that are defined by the spacers 232a,b are capable of interacting with clips 234a,b disposed on other spacers 232a,b or the clip 230 disposed on the first portion 224 of the support arm. Thus, by using the spacers 232a,b in conjunction with the supports 236a,b, it is possible to extend the second portion 228 of the support arm away from the first portion 224 of the support arm to either increase or decrease the overall length of the support arm.

Figure 9:
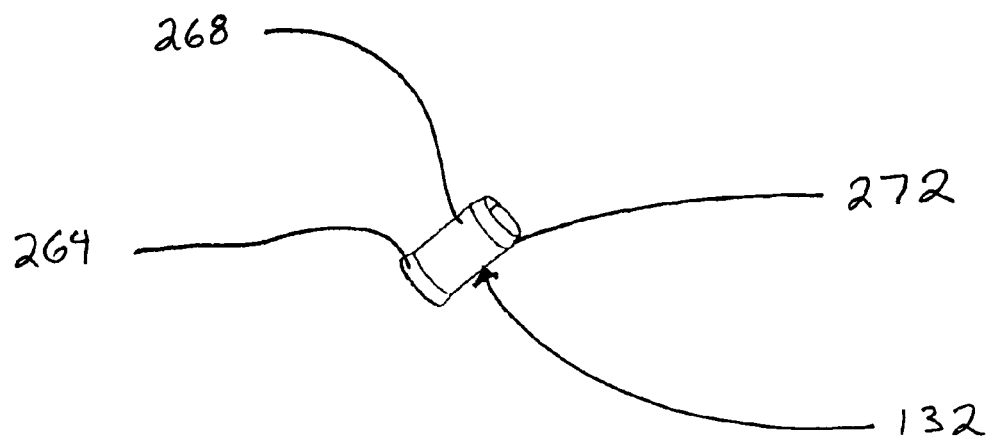
FIG. 9 illustrates an isometric view of the collet shown in FIG. 5 and FIG. 6.

FIG. 9. The outwardly tapered end 264 of the collet 132 allows a support arm to easily enter the body 268 of the collet. However, the inwardly tapered end 272 prevents the support arm from sliding out of or rotating within the collet 132. The collet 132 fits tightly in the housing 128 (shown in FIG. 5), with the inwardly tapered end 272 of the collet 132 resting against the distal end 152 (shown in FIG. 5) of the housing 128. Thus, the collet 132 is capable of maintaining position inside of the housing 128 while preventing the support arm 124 from sliding through the collet 132.

Figure 10:
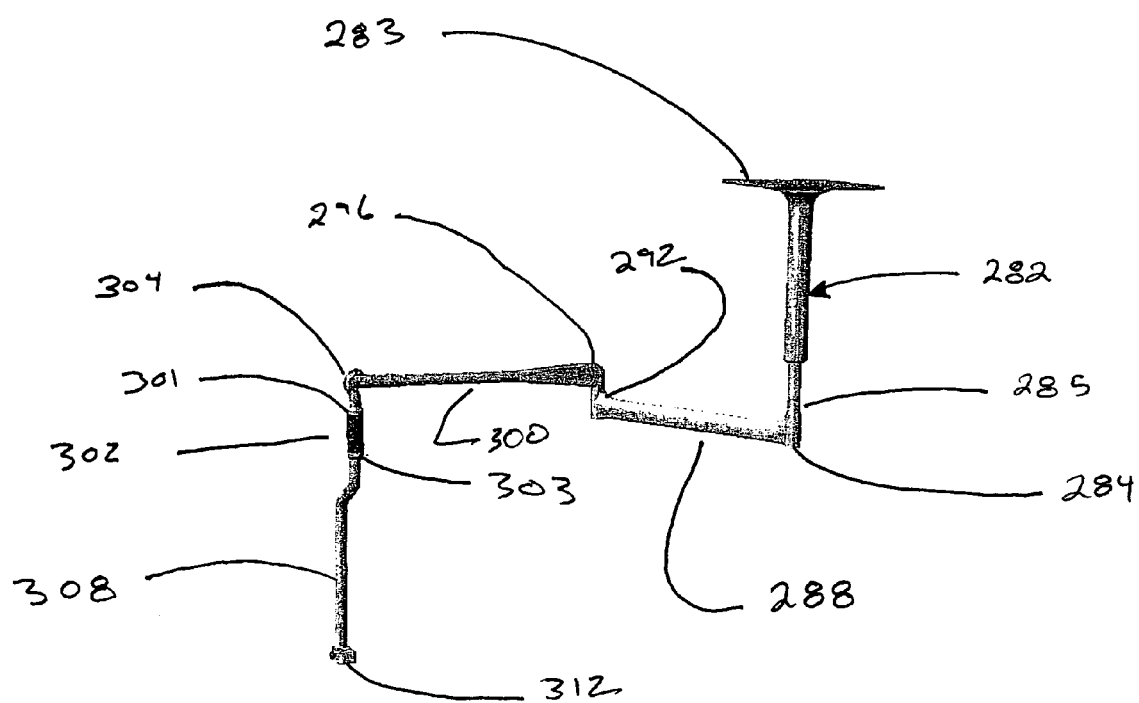
FIG. 10 illustrates an elevational view of a preferred embodiment of an apparatus for supporting medical equipment.

FIG. 10 illustrates an elevational view of a preferred embodiment of an apparatus for supporting medical equipment. In this embodiment, a housing 282 defines a distal end 283 that is adapted to connect to a support structure such as a ceiling. This connection can be accomplished using a mounting plate of the present invention. The distal end 283 of the housing 282 can define one or more protrusions or pins adapted to interact with the mounting plate. Then, by simply inserting the pins into the proper openings in the mounting plate and rotating, the housing 282 can be partially secured. The housing 282 can then be completely secured and prevented from moving by driving pins or other support devices through the distal end 283 and into the mounting plate or support structure.

First support arm 285 extends from the housing, and can be further extended by placing spacers in the distal end 283 of the housing 282. Furthermore, it is preferable that first support arm 285 be prevented from rotating. Therefore, a collet of the present invention, through which the first support arm 285 passes, can be disposed on the interior of the housing 282. Another way in which the first support arm 285 can be prevented from moving rotationally is by splining the interior of the housing 282 and adapting the first support arm 285 to receive the spline.

The first support arm 285 is connected to second support arm 288 at first pivot joint 284.

First pivot joint 284 can utilize self-lubricating polymer bushings to provide a more effective blend of structural integrity, self-lubrication and low running friction than sintered metal bearing or needle bearings. Self-lubricated polymer bushings further enable the system to be installed level and plumb within plus or minus one degree. Second pivot joint 292, which connects second support arm 288 to third support arm 300 can also utilize self-lubricating polymer bushings. First pivot joint 284 and second pivot joint 292 allow for horizontal rotation of the system and increase the flexibility of use.

Third support arm 300 is an articulating counterbalance arm that is connected to second pivot joint 292 through vertically rotating joint 296. Vertically rotating joint 296 allows the system to be further adjusted vertically. Third support arm 300 is connected to an assembly 302 by virtue of support joint 304 and cap 301, and assembly 302 is, in turn, connected to fourth support arm 308 through lower portion 303 of the assembly 302.

The function of assembly 302 is to limit force imparted on support system 280 as well as provide visual and tactile indication of excess force. If strong force were applied to fourth support arm 308, if someone should inadvertently run into fourth support arm 308 for example, then the assembly 302 would flex, causing fourth support arm 308 to move with the force. However, assembly 302 is resilient, so once the force is removed, fourth support arm 308 returns to its original position.

Connector 312 is adapted to receive anyone of a number of medical devices, one of them being an injector head. It is duly recognized that medical devices can vary greatly in weight, and since vertical adjustment of the system is largely determined by third support arm 300, which is a articulating counterbalance arm, it can be possible to load lead weights into fourth support arm 308 to adjust for lighter devices. Then for ease of operation, third support arm 300 should be tuned to accept heavy weights, since additional weight can always be loaded into fourth support arm 308.

Figure 11:
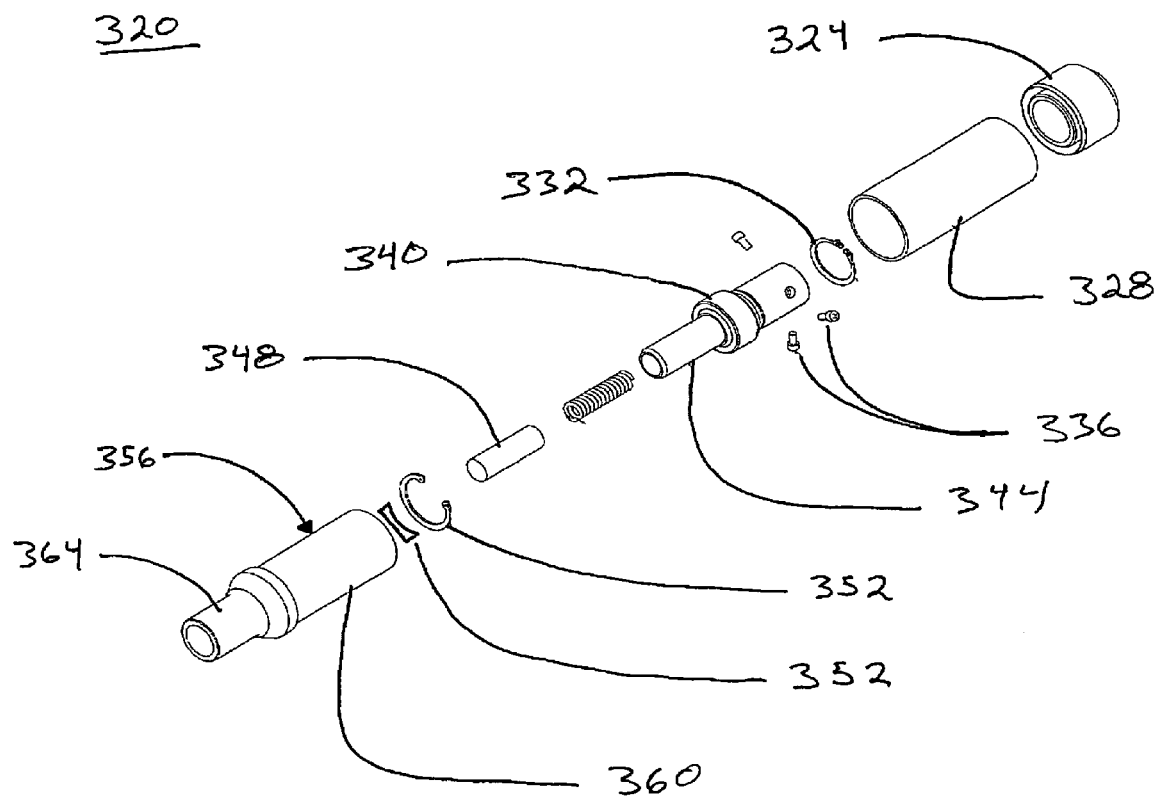
FIG. 11 illustrates an exploded isometric view of an assembly of the present invention.

FIG. 11 illustrates an exploded isometric view of another embodiment of an assembly of the present invention. The assembly 320 comprises a cap 324, which is capable of engaging with a first portion of a support arm. The lower portion 364 of the lower interface 356 is capable of engaging with a second portion of the support arm, so that the assembly is disposed on the support arm. The lower interface 356 also comprises a tubular upper portion 360 that is capable of connecting to the cap 324. Before the cap 324 is connected, however, the sleeve 328 must be fitted over the upper portion 360 of the lower interface 356. Once the sleeve 328 is fitted over the upper portion 360 of the lower interface 356 and the cap 324 is connected to the upper portion 360 of the lower interface, the exterior of the assembly 320 is formed.

The remaining components of the assembly 320 are all intended to be disposed within the exterior of the assembly 320 and act together to allow the assembly 320 to flex. The detent 348, which has a convex tip, is guided into the flat bottom interior of the seat 354, which is inserted in the lower interface 356. The seat 354, besides defining a flat bottom, also defines angled walls that constrict the volume of the seat 354. One skilled in the art will recognize that there are a variety of ways to 'tune' assembly 320 so that it works best for a specific application. For example, adding grease or another form of lubrication to the pieces of assembly 320 that routinely slide against each other, like the seat 354 and detent 348, could promote smooth operation and increased durability.

The spring 344 loads into the holder 340. When the spring 344 and holder 340 are loaded into the lower interface 356, and the detent 348 is previously disposed so that the concave portion of the detent 348 rests against the flat bottom interior of the seat 354, the spring 344 engages the detent 348 so that the detent 348 at least partially compresses the spring 340 and at least a portion of the detent is disposed in the holder 340. Once again, the spring 344 is another aspect of the present invention that can be 'tuned' for the application at hand. For example, depending on the amount of resiliency required, one could replace spring 344 with compressible fluid members, air cylinder, elastomeric members, or other shock absorbing devices.

A standard spherical bearing (not shown), also disposed in holder 340 allows assembly 320 to rock and rotate.

Figure 12:
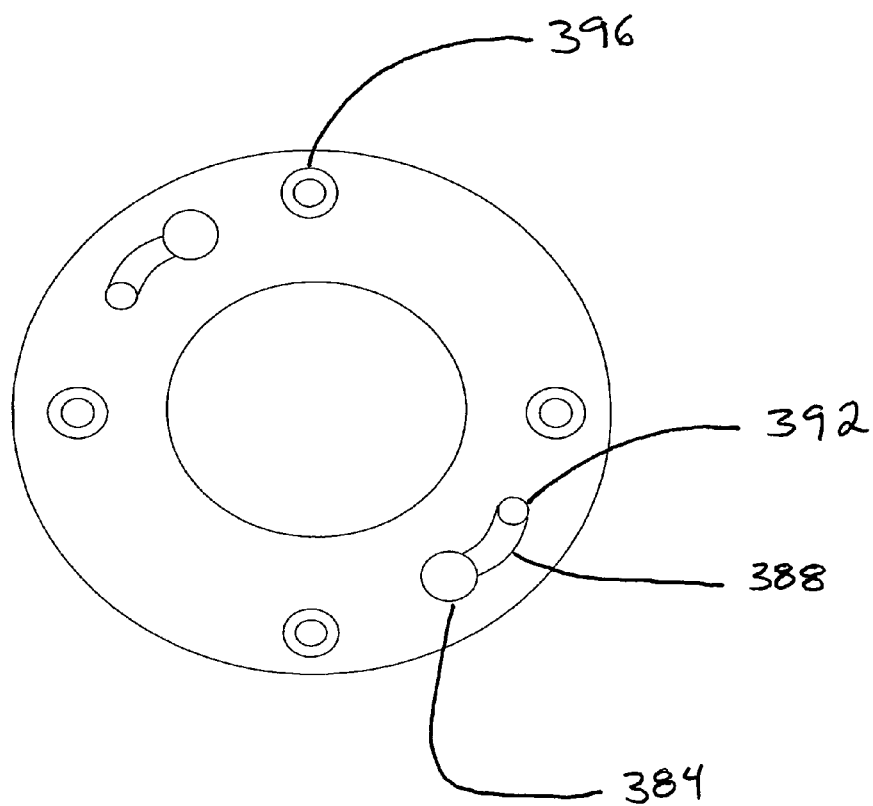
FIG. 12 illustrates a preferred embodiment of a mounting plate of the present invention.

FIG. 12 illustrates a preferred embodiment of a mounting plate of the present invention.

The mounting plate 380 defines an opening 384, a channel 388, and a hole 396. The opening 384 is capable of receiving the bulkhead of a pin disposed on the distal end of a housing. Once the bulkhead of the pin is inserted into opening 384, a rotation of the housing will cause the shaft of the pin to move through channel 388 until it reaches the end 392 of channel 388. After the rotation is completed, the housing can be further secured against the mounting plate by inserting a screw through the distal end of the housing and into hole 396.

This allows the housing, which can be quite heavy, to be manually installed by a single person. Furthermore, it also streamlines installation while still providing ample support that will help prevent the housing from moving vertically or horizontally once installation is complete.

Figure 13:
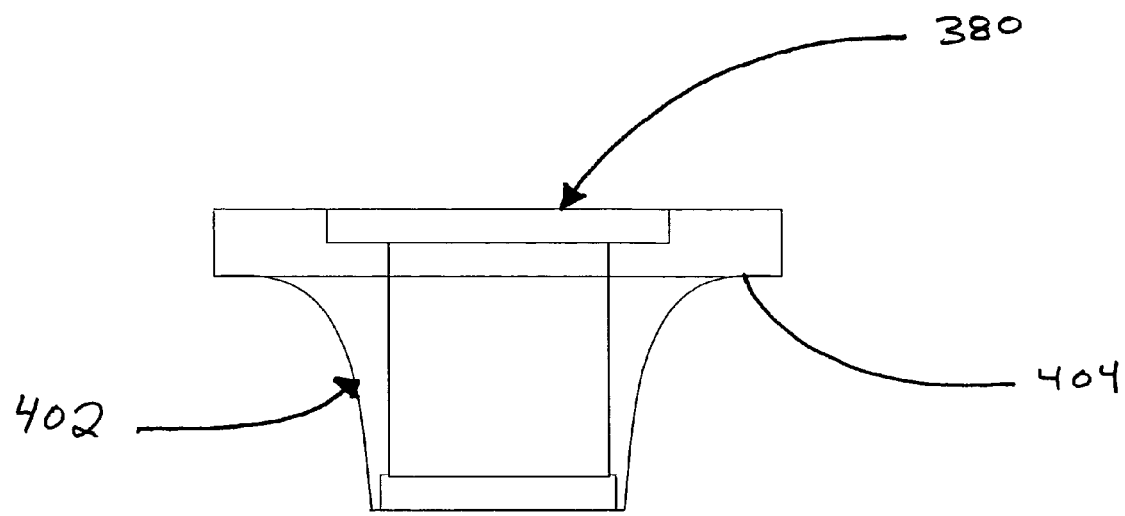
FIG. 13 illustrates an elevational view of an embodiment of a housing interacting with the mounting plate shown in FIG. 12.

FIG. 13 illustrates an embodiment of the mounting plate interacting with the housing. In this embodiment, housing 402 is placed so it partially surrounds mounting plate 380.

Once in place, the housing 402 can be rotated to move the shaft of the pin through channel 388 (shown in FIG. 12). After this is done, the housing is partially secure against the mounting plate allowing for a user to then have two free hands. The user could then drive a screw through a portion of the housing 402 to interact with hole 396 (shown in FIG. 12). Additional support could be added by driving supports through the flange 404 of the housing 402 and into a support structure.

One skilled in the art will recognize several ways in which the support system could be modified to use different securing mechanisms than screws and pins. Also, in another preferred embodiment, the pins are defined by the mounting plate and the openings, channels and holes are defined by the housing.

Although the present invention has been described in detail in connection with the above examples, it is to be understood that such detail is solely for that purpose, and that variations can be made by those skilled in the art without departing from the spirit of the invention. The scope of the invention is indicated by the following claims rather than by the foregoing description. All changes to the present invention that fall within the meaning and range of equivalency of the claims are to be embraced within their scope.

What is claimed is:

1. An apparatus for supporting medical equipment, the apparatus comprising:
   a housing operatively connected to a support structure;
   a first support arm adapted to at least partially fit within the housing and positioned to extend outwardly from the housing; and
   a spacer adapted to fit at least partially within the housing to allow the first support arm to further extend outwardly from the housing;
   the first support arm comprising an abutment member attached to a rearward end thereof to abut a rearward end of the spacer.

2. The apparatus of claim 1 further comprising a plurality of spacers within the housing.

3. An apparatus for supporting medical equipment, the apparatus comprising:
   a housing operatively connected to a support structure;
   a first support arm adapted to at least partially fit within the housing and positioned to extend outwardly from the housing; and
   a collet adapted to fit at least partially within the housing, the collet also adapted to receive and encompass the circumference of the first support arm to prevent the first support arm from sliding rotationally.

* * * * *